United States Patent
Kuechler et al.

(10) Patent No.: US 7,083,762 B2
(45) Date of Patent: Aug. 1, 2006

(54) MULTIPLE RISER REACTOR WITH CENTRALIZED CATALYST RETURN

(75) Inventors: Keith Holroyd Kuechler, Friendswood, TX (US); James R. Lattner, Seabrook, TX (US); Nicolas P. Coute, Houston, TX (US); Jeffrey S. Smith, Seabrook, TX (US); Justin Leonard Krieger, Alexandria, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 527 days.

(21) Appl. No.: 10/338,601

(22) Filed: Jan. 8, 2003

(65) Prior Publication Data

US 2004/0076554 A1  Apr. 22, 2004

Related U.S. Application Data

(60) Provisional application No. 60/419,408, filed on Oct. 18, 2002.

(51) Int. Cl.
*B32B 5/02* (2006.01)
*B32B 27/04* (2006.01)
*C10G 51/06* (2006.01)

(52) U.S. Cl. .................. 422/144; 422/145; 208/74; 208/78; 208/155

(58) Field of Classification Search ............... 422/144, 422/145; 208/74, 78, 155
See application file for complete search history.

(56) References Cited

U.S. PATENT DOCUMENTS

| | | | |
|---|---|---|---|
| 1,421,640 A | 7/1922 | Whitaker et al. | |
| 2,378,236 A | 6/1945 | Miller | 260/652 |
| 2,472,377 A | 6/1949 | Keith | 260/449.6 |
| 2,768,127 A | 10/1956 | Kimberlin, Jr. et al. | 196/55 |
| 2,847,364 A * | 8/1958 | Hirsch | 208/59 |
| 3,205,275 A * | 9/1965 | Johnson | 585/266 |
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |

(Continued)

FOREIGN PATENT DOCUMENTS

EP    0 096 996    12/1983

(Continued)

OTHER PUBLICATIONS

Blackwell et al., "Solid-State NMR of Silicoaluminophosphate Molecular Sieves and Aluminophosphate Materials," *J. Phys. Chem.*, vol. 92, pp. 3965-3970, New York (1998).

(Continued)

*Primary Examiner*—N. Bhat

(57) ABSTRACT

The present invention is directed to a hydrocarbon conversion apparatus and process. The apparatus comprises the following: a plurality of riser reactors, each having a first end into which a catalyst is fed, a second end through which the catalyst can exit, and optionally a center axis extending therebetween. The apparatus also includes a separation zone having a plurality of inlets, each inlet not being oriented along the center axes of the riser reactors, the separation zone being provided to separate the catalyst from products of a reaction conducted in the hydrocarbon conversion apparatus. A plurality of deviating members are also provided, each deviating member being in fluid communication between the second end of a respective riser reactor and a respective inlet of the separation zone. The apparatus also includes a catalyst retention zone provided to contain catalyst, which is fed to the riser reactors. A catalyst return is in fluid communication between the separation zone and the catalyst retention zone.

57 Claims, 4 Drawing Sheets

U.S. PATENT DOCUMENTS

| | | | | |
|---|---|---|---|---|
| 3,645,992 | A | 2/1972 | Elston | 260/80.78 |
| 3,764,634 | A | 10/1973 | Ozawa et al. | 260/683 R |
| 3,886,060 | A * | 5/1975 | Owen | 208/120.01 |
| 3,894,935 | A * | 7/1975 | Owen | 208/78 |
| 3,959,117 | A | 5/1976 | Bunn, Jr. et al. | 208/113 |
| 4,076,698 | A | 2/1978 | Anderson et al. | 526/348.6 |
| 4,076,796 | A | 2/1978 | Reh et al. | 423/659 |
| 4,134,926 | A | 1/1979 | Tsao et al. | 260/682 |
| 4,138,440 | A | 2/1979 | Chang et al. | 260/668 R |
| 4,229,608 | A | 10/1980 | Chen et al. | 585/640 |
| 4,243,691 | A | 1/1981 | Mohlenkamp, Jr et al. | 426/649 |
| 4,302,565 | A | 11/1981 | Goeke et al. | 526/88 |
| 4,310,411 | A * | 1/1982 | Wilkening | 208/153 |
| 4,379,123 | A | 4/1983 | Daviduk et al. | 422/142 |
| 4,440,871 | A | 4/1984 | Lok et al. | 502/214 |
| 4,499,327 | A | 2/1985 | Kaiser | 585/640 |
| 4,500,423 | A * | 2/1985 | Krug et al. | 208/161 |
| 4,547,616 | A | 10/1985 | Avidan et al. | 585/640 |
| 4,590,320 | A | 5/1986 | Sapre | 585/324 |
| 4,659,685 | A | 4/1987 | Coleman, III et al. | 502/113 |
| 4,677,242 | A | 6/1987 | Kaiser | 585/638 |
| 4,677,243 | A | 6/1987 | Kaiser | 585/638 |
| 4,683,121 | A | 7/1987 | Goudriaan et al. | 422/197 |
| 4,688,808 | A | 8/1987 | Iijima | 277/223 |
| 4,752,651 | A | 6/1988 | Kaiser | 585/640 |
| 4,814,541 | A | 3/1989 | Lewis | 585/640 |
| 4,853,105 | A * | 8/1989 | Herbst et al. | 208/74 |
| 4,861,938 | A | 8/1989 | Lewis et al. | 585/640 |
| 4,873,390 | A | 10/1989 | Lewis et al. | 585/638 |
| 4,929,798 | A | 5/1990 | De Lasa | 585/922 |
| 4,973,792 | A | 11/1990 | Lewis et al. | 585/638 |
| 5,095,163 | A | 3/1992 | Barger | 585/640 |
| 5,157,181 | A | 10/1992 | Stine et al. | 585/640 |
| 5,157,193 | A | 10/1992 | Miller | 585/640 |
| 5,191,141 | A | 3/1993 | Barger et al. | 585/640 |
| 5,271,905 | A | 12/1993 | Owen et al. | 422/142 |
| 5,273,094 | A | 12/1993 | Chavet | 422/197 |
| 5,278,345 | A | 1/1994 | Janssen et al. | 585/640 |
| 5,343,830 | A | 9/1994 | Alexander et al. | 122/4 D |
| 5,475,182 | A | 12/1995 | Janssen | 585/640 |
| 5,672,798 | A * | 9/1997 | Zhang et al. | 585/467 |
| 5,714,662 | A | 2/1998 | Vora et al. | 585/640 |
| 5,714,663 | A | 2/1998 | Serrand et al. | 585/648 |
| 5,723,094 | A | 3/1998 | Sunavala | 422/197 |
| 5,811,621 | A | 9/1998 | Van Dijk | 585/639 |
| 5,892,079 | A | 4/1999 | Wilson, Jr. | 556/11 |
| 5,904,880 | A | 5/1999 | Sun | 252/373 |
| 5,907,076 | A | 5/1999 | Ou et al. | 585/800 |
| 5,925,586 | A | 7/1999 | Sun | 502/62 |
| 5,925,800 | A | 7/1999 | Sun et al. | 585/640 |
| 5,927,063 | A | 7/1999 | Janda et al. | 60/39.02 |
| 5,932,512 | A | 8/1999 | Sun | 502/214 |
| 5,952,538 | A | 9/1999 | Vaughn et al. | 585/640 |
| 5,958,222 | A | 9/1999 | Radcliffe et al. | 208/163 |
| 5,960,643 | A | 10/1999 | Kuechler et al. | 62/620 |
| 5,962,762 | A | 10/1999 | Sun et al. | 585/640 |
| 5,972,203 | A | 10/1999 | Smith et al. | 208/113 |
| 6,004,898 | A | 12/1999 | Sun | 502/214 |
| 6,005,155 | A | 12/1999 | Sun | 585/640 |
| 6,023,005 | A | 2/2000 | Lattner et al. | 585/639 |
| 6,040,264 | A | 3/2000 | Sun et al. | 502/214 |
| 6,045,688 | A | 4/2000 | Ruottu et al. | 208/113 |
| 6,046,371 | A | 4/2000 | Wu et al. | 585/638 |
| 6,046,373 | A | 4/2000 | Sun | 585/640 |
| 6,051,745 | A | 4/2000 | Wu et al. | 585/638 |
| 6,051,746 | A | 4/2000 | Sun et al. | 585/640 |
| 6,057,261 | A | 5/2000 | Sun | 502/341 |
| 6,166,282 | A | 12/2000 | Miller | 585/638 |
| 6,287,522 | B1 | 9/2001 | Lomas | 422/144 |
| 2003/0004384 | A1 | 1/2003 | Coute et al. | 585/639 |
| 2004/0059171 | A1 * | 3/2004 | Brookhart | 585/638 |
| 2004/0064007 | A1 * | 4/2004 | Beech et al. | 585/639 |
| 2005/0152814 | A1 * | 7/2005 | Lattner et al. | 422/129 |

FOREIGN PATENT DOCUMENTS

| | | |
|---|---|---|
| EP | 0 541 915 | 5/1993 |
| EP | 0 844 021 | 5/1998 |
| EP | 1 046 695 | 10/2000 |
| EP | 1 053 783 | 2/2003 |
| WO | WO 99/01219 | 1/1999 |
| WO | WO 01/04076 | 1/2001 |
| WO | WO 01/85872 | * 11/2001 |

OTHER PUBLICATIONS

Bos et al., "Conversion of Methanol to Lower Olefins. Kinetic Modeling, Reactor Simulation, And Selection," *Ind. Eng. Chem. Res.*, vol. 34, Amsterdam, The Netherlands, pp. 3808-3816, (1995).

Knapik et al., "New FCC Technology," *UOP*, Des Plaines, Illinois, pp. 1-24, (1995).

* cited by examiner

MULTIPLE RISER REACTOR WITH CENTRALIZED CATALYST RETURN

This application claims priority to U.S. Ser. No. 60/419,408, filed Oct. 18, 2002, which is fully incorporated herein by reference. The present invention relates to a reactor useful in hydrocarbon conversion processes and particularly in oxygenate to olefin conversion reactions.

Field of the Invention

BACKGROUND OF THE INVENTION

When converting a feedstock containing a hydrocarbon to a product in an industrial reactor, it is desirable to maximize the production of a desired product or products, and to control, typically to minimize, the production of by-products. One type of reactor useful for conducting hydrocarbon conversion reactions is a fluidized bed reactor, wherein solid catalyst particles are suspended in a fluidized state during contact with the feedstock and other vapor materials. These types of reactors usually have a cylindrical reactor geometry. One method for reducing the production of by-products in a fluidized bed reactor involves operating in a hydrodynamic flow regime such that the superficial gas velocity obtains a velocity high enough to cause the net flow of catalyst in the reactor to flow in the same direction as the flow of the feedstock and other vapors, i.e., the feedstock and other vapors essentially carry the catalyst particles along with them. These flow regimes are known to those skilled in the art as the fast-fluidized bed and riser regimes, more generally as the transport regime, and are preferred in reaction systems in which a more plug flow reactor type is desired.

In general, for a given reactor cross sectional area (which in a cylindrical reactor geometry is proportional to the diameter, and more generally to a characteristic width), the catalyst concentration in a fluidized bed reactor decreases with increasing gas superficial velocity. Higher gas superficial velocities generally require taller reactor heights to allow a given amount of feedstock to contact a required amount of catalyst. These higher gas superficial velocities necessitate a higher aspect ratio (the ratio of a reactor height to its diameter or characteristic width) of the reactor. Further, in many cases it is desired to make a fluidized reactor with a very large cross-sectional area to enable very large throughputs of feedstock in a single reactor facility. However, increasing fluid bed diameter, particularly in the transport regime, also necessitates increased reactor height. This increased height is required because a certain minimum reactor height, in terms of a minimum aspect ratio, is required to achieve a fully developed flow pattern, which approximates plug flow reactor behavior. At the exit and, particularly, at the entrance of a transport regime fluidized bed reactor, unsteady state momentum effects dominate hydrodynamic behavior (e.g., the energy required for the feedstock vapors to pick up and accelerate the solid catalyst against the force of gravity) in a manner not conducive to obtaining approximate plug flow behavior. Not until these momentum effects are dampened out by progressing along the reactor height will a well behaved, approximately plug flow fluid/solid flow pattern emerge. Finally, should the use of lower activity catalysts be desired in the transport regime, aspect ratios must also increase to provide desired higher feedstock conversion.

Unfortunately, high aspect ratio transport fluid bed reactors are difficult and expensive to construct and maintain. They are expensive because they must have at the top a very large, heavy separation vessel, often filled with heavy equipment, to capture and manage the flowing catalyst and reactor product. As the reactor increases in height (aspect ratio), more expensive support structures may be required. In certain areas of the world where inclement, especially windy weather occurs routinely, even more structural support is required, and certain aspect ratios are not economic. Multiple, complete and independent reactor systems with independent separation vessels are required. With these multiple, complete and independent reactor systems come attendant multiplication of costs.

Thus, a need exists in the art for a reactor that can provide the desired aspect ratio without necessitating an unwieldy height, forcing a width in which the desired, fully developed flow regime may never be obtained, or without resulting to multiple, independent reactor systems.

SUMMARY OF THE INVENTION

The present invention provides a solution to the currently existing need in the art by providing a shorter hydrocarbon conversion apparatus while maintaining a high aspect ratio in the riser reactors. The hydrocarbon conversion apparatus includes a plurality of riser reactors, each of which is in fluid communication with a respective deviating member, which deviates the flow of product, unreacted feed, and catalyst from the top of the riser reactor to a plurality of side inlets on a separation zone. Preferably, the inlets are formed in the upper section of the separation zone. By deviating the flow of material from the top of the riser reactors through inlets oriented in the upper section of the separation zone, the overall height of the separation zone, and thus the height of the overall hydrocarbon conversion apparatus, may be advantageously reduced.

Additionally, by orienting the riser reactors adjacent the vertically extending sides of the separation zone, rather than orienting the riser reactors beneath the separation zone, the present invention provides the additional advantage of increasing the number of possible riser reactors in a given hydrocarbon conversion apparatus. By increasing the number of riser reactors in a given hydrocarbon conversion apparatus, the quantity of product formed per unit time is increased.

In one embodiment of the present invention, the hydrocarbon conversion apparatus comprises a plurality of riser reactors, each having a first end into which a catalyst may be fed, a second end through which the catalyst can exit, and a center axis or centroid line extending therebetween. A separation zone having a plurality of inlets, each inlet preferably not being oriented along the center axes of the riser reactors, is provided to separate the catalyst from products of a reaction conducted in the hydrocarbon conversion apparatus. A plurality of deviating members is also provided, each deviating member being in fluid communication between the second end of a respective riser reactor and a respective inlet of the separation zone. The apparatus also includes a catalyst retention zone provided to contain catalyst, which is then fed to the riser reactors, and a catalyst return in fluid communication between the separation zone and the catalyst retention zone.

The invention is also directed to a hydrocarbon conversion apparatus including a plurality of riser reactors, each having a first end into which a catalyst is fed and a second end through which the catalyst can exit the riser reactor. A separation zone is provided to separate the catalyst from products of a reaction conducted in the hydrocarbon conversion apparatus, the separation zone including a plurality of inlets. The apparatus also includes a plurality of deviating members, each deviating member being oriented to deviate a flow of material from the second end of a respective riser reactor toward a respective inlet. At least one catalyst return is in fluid communication with the separation zone and the first ends of the riser reactors, the catalyst return being provided to transfer the catalyst from the separation zone to the first ends of the riser reactors.

The invention is also directed to a hydrocarbon conversion process including: (a) contacting a fluidizable catalyst with a fluidizing agent to fluidize the fluidizable catalyst; (b) feeding the catalyst and a feed to a plurality of riser reactors, the plurality of riser reactors being part of a single hydrocarbon conversion apparatus; (c) contacting the feed with the catalyst in the plurality of riser reactors under conditions effective to convert the feed to a product; (d) directing the product and the catalyst through a plurality of deviating members each deviating member being positioned to deviate a flow of the product and the catalyst from an outlet of a respective riser reactor to a separation zone; (e) separating the catalyst from the product in the separation zone, the separation zone being in fluid communication with the plurality of deviating members; (f) returning the catalyst from the separation zone to the plurality of riser reactors; and (g) repeating steps (a) to (f).

In another embodiment, the invention is to a hydrocarbon conversion apparatus including a plurality of riser reactors, each having a first end for receiving catalyst and a second end through which the catalyst and a product can exit. A plurality of deviating members are provided, each deviating member being associated with a respective riser reactor. A separation zone having at least one side is provided to separate the catalyst from the product, wherein the separation zone includes a plurality of inlets, each inlet being associated with a respective deviating member, and wherein the inlets are oriented on the side of the separation zone. The apparatus also includes a catalyst return coupled to a plurality of arms, the catalyst return and arms being in fluid communication between the separation zone and the first ends of the plurality of riser reactors.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

The present invention provides a hydrocarbon conversion apparatus including a plurality of riser reactors, each of which is in fluid communication with a respective deviating member. Each deviating member deviates the flow of product, unreacted feed, and catalyst from the top of a respective riser reactor to one of a plurality of inlets on the separation zone. Preferably the inlets are formed on the side of the upper section of the separation zone. By deviating the flow of material from the top of the riser reactors through inlets oriented in the upper section of the separation zone, the overall height of the separation zone, and thus the overall height of the hydrocarbon conversion apparatus, may be advantageously reduced. The present invention provides the additional advantage of allowing the size of the separation vessel to be reduced because the top of the riser reactors are not required to extend inside the separation vessel.

Figure 1:
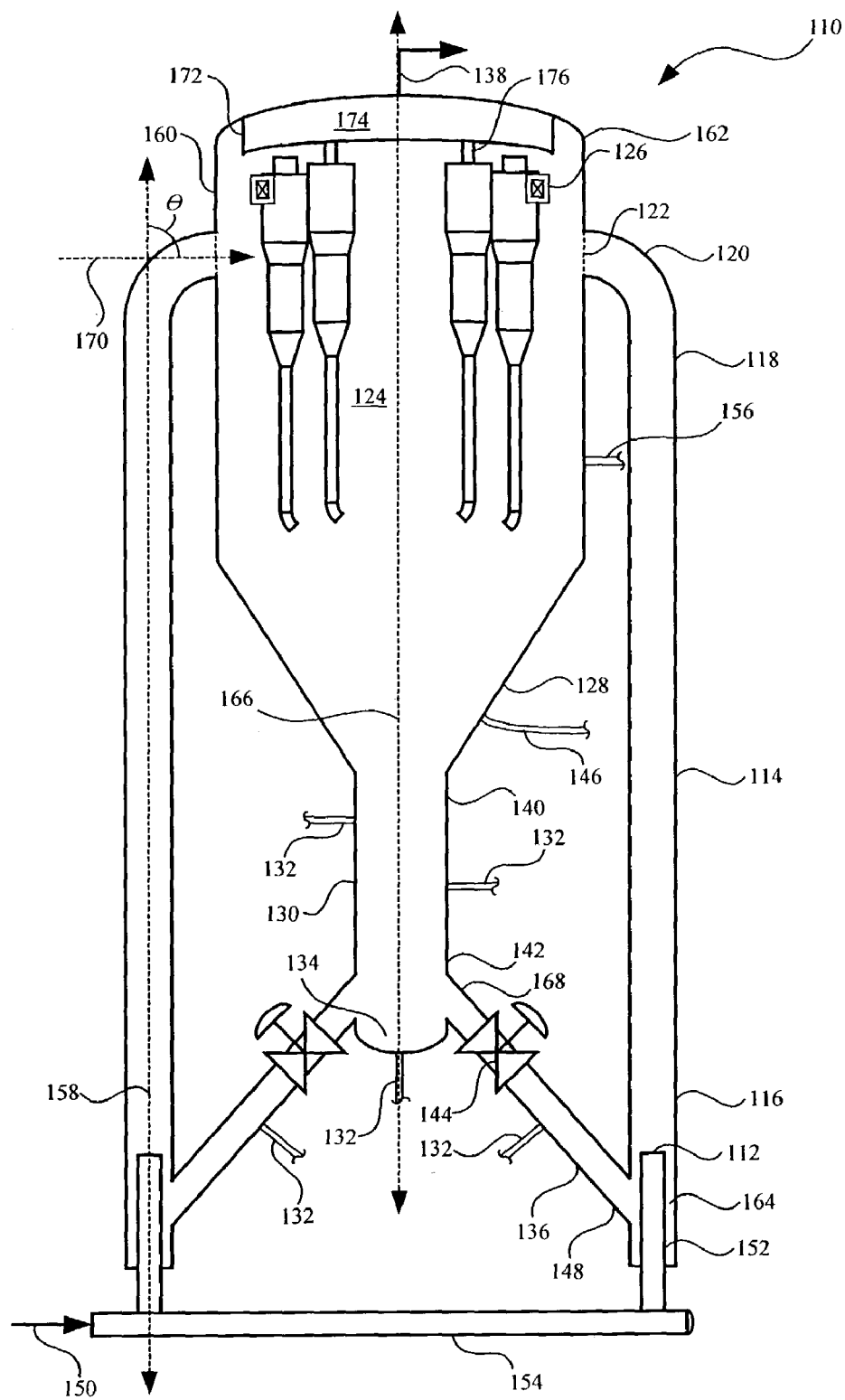
FIG. 1 presents a partial cross sectional view of a hydrocarbon conversion apparatus of the present invention.

FIG. 1 presents a partial cross sectional view of a hydrocarbon conversion apparatus (HCA), generally designated 110, in accordance with one embodiment of the present invention. The HCA 110 comprises a shell 160, separation zone 124, a plurality of riser reactors 114, a feed distributor 154, and a catalyst return 130. With continuing reference to FIG. 1, the shell 160 defines the separation zone 124 in which a product of the hydrocarbon conversion reaction is separated from the catalyst, which catalyzes the hydrocarbon conversion reaction. Shell 160 and separation zone 124 include a first end 162 and a second end 128. The separation zone 124 preferably includes one or more separation devices 126, which are used to separate the products from the catalyst. The separation devices 126 may be cyclonic separators, filters, screens, impingement devices, plates, cones or any other device, which would separate the catalyst from the product of the conversion reaction. The separation devices 126 shown in FIG. 1 are cyclonic separators. In other embodiments, not illustrated, the separation devices are positioned externally to the separation zone 124, outside of the shell defining the separation zone 124, or a combination of externally and internally positioned separation devices.

Riser reactors 114 extend adjacent to shell 160 and the separation zone 124. Each riser reactor 114 includes a first end 116 into which the catalyst and feed are fed to conduct the hydrocarbon conversion reaction. If the riser reactor 114 is a cylindrical form, as shown in FIG. 1, a center axis 158 extends between the first end 116 and the second end 118. If the riser reactor lacks a central axis, e.g., is not cylindrical, conical, etc., a centroid line perpendicular to a cross-sectional plane of the riser reactor extends between the first and second ends. Preferably, the separation zone 124 is a cylindrical form having a center axis 166, which is preferably parallel to the center axis 158 of riser reactors 114. Each riser reactor 114 further includes a second end 118 through which the catalyst, products and unreacted feed, if any, exit the riser reactor 114. The first end 116 of each riser reactor 114 terminates in a mouth 164 through which the catalyst is fed into the riser reactor 114. The number of riser reactors 114 employed in the HCA 110 varies depending on the hydrocarbon conversion process to be conducted in the apparatus 110. The apparatus 110 can contain two, three, four, five, six or even more than six riser reactors 114.

The geometry of the riser reactors 114 may vary widely. In the embodiment in FIGS. 1 and 2, the geometry is comprised of a cylindrical member. Optionally, the geometry of the riser reactors is comprised of a single, right frustum of a cone. Other suitable geometric shapes include, but are not limited to, triangular prisms and frusta of pyramids, rectangular and square wedges and frusta of pyramids, and pentagonal, hexagonal, septagonal and octagonal prismatoids and frusta thereof, general and right. Further non-limiting examples include various polyhedrons, such as a tetrahedron, an octohedron, a dodecahedron or an icosahedron, and conical spheres and spherical sectors, and torus and barrels in their circular, elliptical or parabolic forms, and frusta thereof, general and right. Multiple occurrences of any of these geometric shapes defining the riser reactor and/or the associated separation zone are also within the scope of an apparatus of the present invention.

In accordance with the present invention, at least one riser reactor 114, preferably a plurality of riser reactors 114 are oriented externally to the shell 160. If shell 160 is substantially cylindrical, riser reactors 114 are positioned beyond the maximum diameter defined by shell 160. Riser reactors 114 preferably are not positioned directly underneath separation zone 124. In one embodiment, the riser reactors 114 are positioned adjacent to separation zone 124. In this embodiment, the second ends 118 of each riser reactor 114 enter separation zone 124 above the second end 128 of separation zone 124.

Second end 118 of each riser reactor 114 preferably is in fluid communication with a deviating member 120. The deviating member 120 preferably is a curved pipe, elbow, or other conduit device adapted to receive catalyst, products and unreacted feed, if any, that exits riser reactor 114 through second end 118. The deviating member 120 deviates the flow of the catalyst, products and unreacted feed from the second end of the riser reactor 114 toward inlet 122 on the side wall(s) of shell 160. Preferably, the inlet 122 is not oriented along the center axis 158 (or centroid line of a riser reactor lacking a center axis) of riser reactor 114. Preferably, the deviating member provides a deviating angle of greater than 0 degrees. Preferably, at least one of the deviating members has a deviation angle of at least 10, at least 20, at least 30 or at least 45 degrees, more preferably at least 60, at least 80 or at least 90 degrees. The deviation angle is defined herein as the angle that the flow of catalyst, products and unreacted feed, if any, is deviated by deviating member 120 from the second end 118 of riser reactor 114 to inlet 122. In FIG. 1, the deviation angle is illustrated by deviation angle θ, which is defined by center axis 158 of a riser reactor (or corresponding centroid line of a riser reactor lacking a center axis) and the entry flow path, shown by arrow 170. In FIG. 1, the deviation angle θ is approximately 90 degrees.

Figure 6:
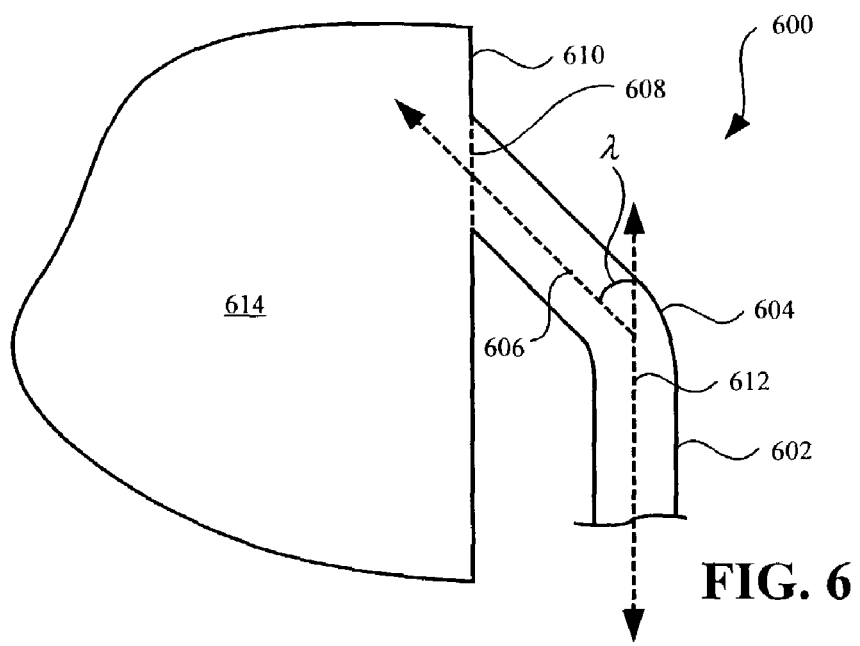
FIG. 6 presents a partial cross sectional view of a deviating member providing a deviation angle of less than 90 degrees.

FIG. 6 illustrates another embodiment, wherein the deviating member assembly, generally designated by arrow 600, provides a deviation angle of less than 90 degrees. As shown in FIG. 6, a riser reactor 602 having a center axis 612 (or centroid line if the riser reactor lacks a center axis) is in fluid communication with a deviating member 604, which deviates the flow of catalyst, product and unreacted feed, if any, to inlet 608 defined by shell 610. Shell 610 also defines separation zone 614, as discussed above. However, unlike the previously-described embodiments, the deviation angle is less than 90 degrees. In FIG. 6, the deviation angle λ is defined by center axis 612 of a riser reactor 602 (or corresponding centroid line of a riser reactor lacking a center axis) and the entry flow path, shown by arrow 606. In FIG. 6, the deviation angle λ is approximately 45 degrees. Erosion is advantageously reduced by providing a deviating member, which defines a deviation angle of less than 90 degrees. In terms of ranges, in one embodiment, the deviation angle is from about 10 to about 90 degrees, more preferably from about 30 to about 90 degrees and most preferably from about 45 to about 90 degrees. In other embodiments, the deviation angle is greater than 90, greater than 100, or greater than 120 degrees.

One embodiment of the present invention, not shown, includes a second plurality of riser reactors oriented underneath the separation zone. Each of the second plurality of riser reactors includes first and second ends and a second center axis extending therebetween. The separation zone includes a plurality of second inlets, each second inlet being oriented along a respective second center axis. Each of the second plurality of riser reactors optionally extends inside the separation zone. In this embodiment, the number of riser reactors for a given separation zone may be greatly increased. Accordingly, the amount of product formed in a single hydrocarbon conversion apparatus can also be significantly increased.

Reverting to FIG. 1, the size of the riser reactors 114 depends on parameters such as superficial gas velocity, solids hydrodynamics, pressure, and production capacity of the desired hydrocarbon conversion process. In the present invention, each riser reactor 114 desirably has a height from 10 meters to 70 meters and a width (or diameter) of one meter to three meters. All of the riser reactors 114 have a similar height from their first ends 116 through their second ends 118. Desirably, the heights of the riser reactors 114 vary by no more than 20% from one riser reactor 114 to another riser reactor 114. More desirably, the heights vary by no more than 10% and, most desirably, the heights vary by no more than 1%.

In one embodiment of the present invention, each of the riser reactors 114 has a similar cross sectional area along its entire height. Desirably, each of the riser reactors has a cross sectional area of no greater than 12 m$^2$. More desirably, each of the riser reactors has a cross sectional area of no greater than 7 m$^2$. Most desirably, each of the riser reactors has a cross sectional area of no greater than 3.5 m$^2$. Desirably, the cross sectional areas of the riser reactors vary by no more than 20% from one riser reactor to another riser reactor. More desirably, the cross sectional areas of the riser reactors vary by no more than 10% and, most desirably, the cross sectional areas of the riser reactors vary by no more than 1%. If one or more riser reactors have both a largest and a smallest cross-sectional area at different points along the height of riser reactors, desirably the largest cross-sectional areas of the riser reactors vary by no more than 20% from one riser reactor to another riser reactor, and the smallest cross-sectional areas of the riser reactors vary by no more than 20% from one riser reactor to another riser reactor. More desirably, the largest cross sectional area of one riser reactor varies by no more than 10% from the largest cross sectional area of another riser reactor and the smallest cross sectional area varies by no more than 10% from the smallest cross sectional area of another riser reactor. Most desirably, the largest cross sectional area of one riser reactor varies by no more than 1% from the largest cross sectional area of another riser reactor and the smallest cross sectional area varies by no more than 1% from the smallest cross sectional area of another riser reactor. Preferably each of the riser reactors has a width (or diameter) of from 1 to 3 meters.

Desirably, the cross sectional area of each riser reactor varies by no more than 50% along its entire height. More desirably, the cross sectional area of each riser reactor varies by no more than 30% along its entire height and, most desirably, the cross sectional area of each riser reactor varies by no more than 10% along its entire height.

In one embodiment, to provide a feed to the riser reactors 114, at least one feed distributor 154 is positioned near the first ends 116 of the riser reactors 114. The feed distributor 154 receives a feed stream from a feed providing line 150 and directs the feed to one or more of the riser reactors 114. In another embodiment, not shown, more than one feed distributor 154 is employed adjacent the first ends 116 of the riser reactors 114 to provide feed in various states, e.g., one feed distributor may provide feed in a vapor form while a second feed distributor may provide feed in a liquid form. Each feed distributor 154 includes a body from which a plurality of necks 152 extend. Each riser reactor 114 has at least one associated neck 152. Each neck 152 terminates in a head 112. Each head 112 of each neck 152 is positioned adjacent to the first end 116 of each riser reactor 114. Desirably, each head 112 extends upwardly into each riser reactor 114. More desirably, each head 112 is positioned at or above the mouth 164 at the first end 116 of each riser reactor 114. Feed distributor 154 may include an optional flow control device, not shown, positioned on feed distributor 154 to control the amount of feed to each neck 152 or a flow control device may be positioned on each neck 152. The flow control device can also be employed to measure flow as well as control it. Further, a nozzle, not shown, may be positioned on each head 112 to further control the distribution of the feed to each riser reactor 114. Additionally, each head 112 may be fitted with a screening, plunger or other device, not shown, to prevent back flow of catalyst into any of necks 152 of feed distributor 154.

Figure 2:
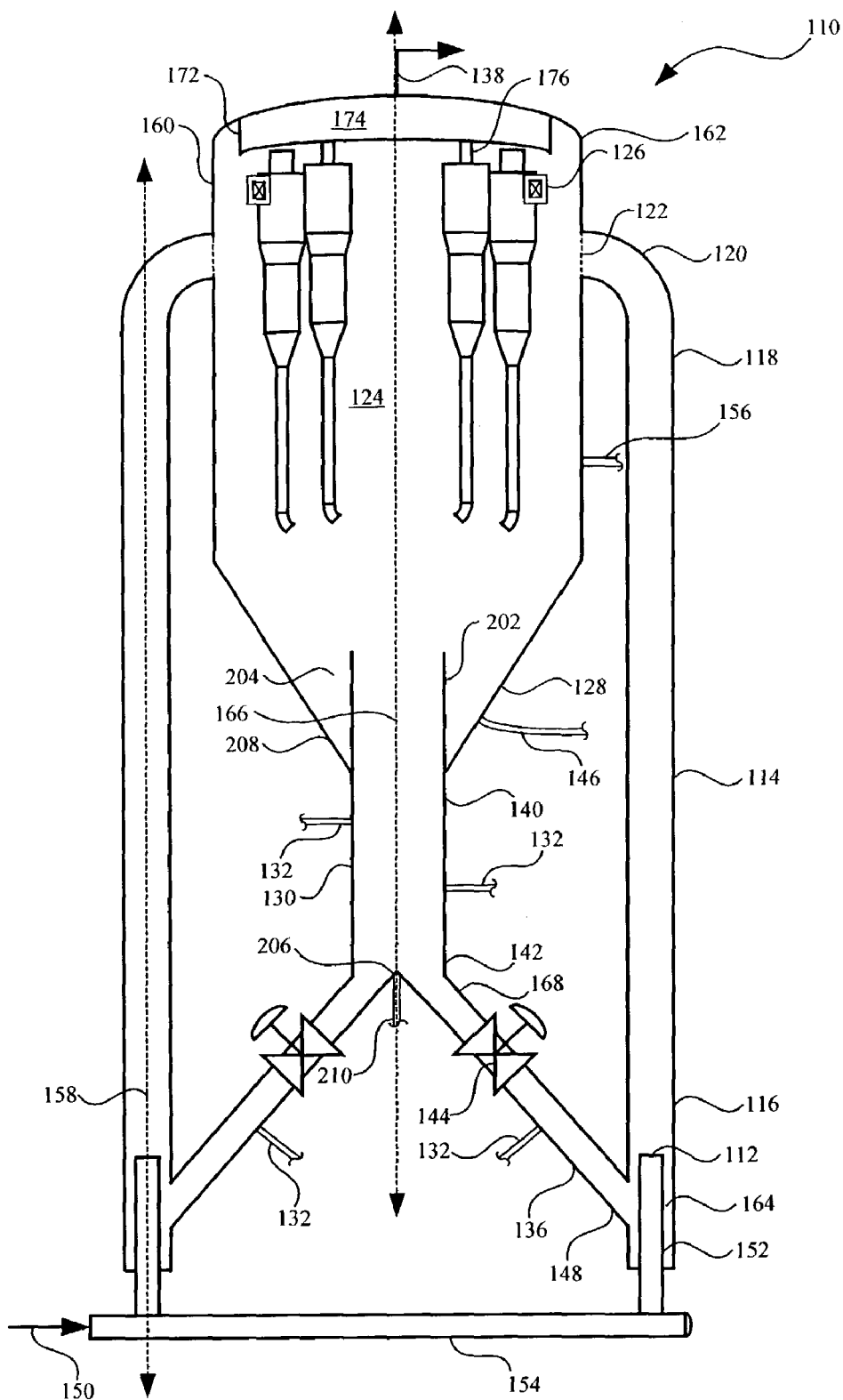
FIG. 2 presents a partial cross sectional view of another embodiment of the hydrocarbon conversion apparatus of the present invention.

At least one catalyst return 130 provides fluid communication between the separation zone 124 of shell 160 and the riser reactors 114. The apparatus 110 may include one, two, three, four, five, six or more catalyst returns 130, although only a single catalyst return 130 is illustrated in FIGS. 1 and 2. If a plurality of catalyst returns are desired, each of the catalyst returns preferably is adapted to deliver catalyst from the separation zone directly to each of the respective riser reactors. Typically, although not necessarily, a single catalyst return 130, which is centrally oriented with respect to the riser reactors 114, is used. In this embodiment, the single catalyst return is in fluid communication with a plurality of arms 136. As shown in FIG. 1, a single catalyst return 130 is positioned centrally in relation to the riser reactors 114. The catalyst return 130 has a first end 140 and a second end 142. The first end 140 of the catalyst return 130 opens into the second end 128 of shell 160 and the second end 142 of catalyst return 130 opens to a series of arms 136 adapted to deliver catalyst to the first ends 116 of riser reactors 114.

The arms 136 extend from the catalyst return 130 to each of the riser reactors 114 and provide fluid communication between the catalyst return 130 and the riser reactors 114. Each arm includes a first end 168 adjacent the catalyst retention zone 134 and catalyst return 130, and a second end 148 adjacent the riser reactor 114. Catalyst flows through each arm 136 from the first end 168 to the second end 148. The number of arms 136 preferably will correspond to the number of riser reactors 114 with each riser reactor having at least one corresponding arm 136. Flow of catalyst through the catalyst return 130 optionally is controlled through the use of flow control device(s) 144 positioned on the catalyst return 130 and/or on each arm 136. The flow control devices may be any type of flow control devices currently in use in the art to control catalyst flow through catalyst transfer lines. If employed, the flow control device 144 is desirably a ball valve, a plug valve or a slide valve.

In the embodiment shown in FIG. 1, the second end 142 of the catalyst return 130 and the arms 136 define a catalyst retention zone 134. The arms 136 open to the catalyst retention zone 134. The catalyst retention zone 134 is provided to retain catalyst, which is used to catalyze the hydrocarbon conversion reaction, which is conducted in the apparatus 110. As one of skill in the art will appreciate, the boundary between the catalyst retention zone 134 and the catalyst return 130 is fluid and depends, at least in part, on the level of catalyst contained in the catalyst retention zone 134 and the arms 136.

At least one fluidizing agent distributor 132 is positioned beneath the catalyst retention zone 134. The fluidizing agent distributor 132 includes a conduit into which a fluidizing agent is fed to fluidize a fluidizable catalyst in the catalyst retention zone 134 and the catalyst return 130. Additional fluidizing agent distributors 132, as shown in FIG. 1, may also be positioned on the catalyst return 130 and/or on one or more of the arms 136 to further fluidize catalyst contained therein. Optionally, the catalyst retention zone 134 includes a disperser, not shown, positioned in the catalyst retention zone and provided to disperse the fluidizing agent in the catalyst retention zone to facilitated fluidization of the catalyst therein. For example, the disperser could be a device selected from the group consisting of a grid, a screen and a perforated plate. Preferably, at least one disperser extends in a plane perpendicular to the center axis 166 of the separation zone 124 (or centroid line if the separation zone lacks a center axis) and is oriented above one or more fluidizing agent distributors 132.

Figure 7:
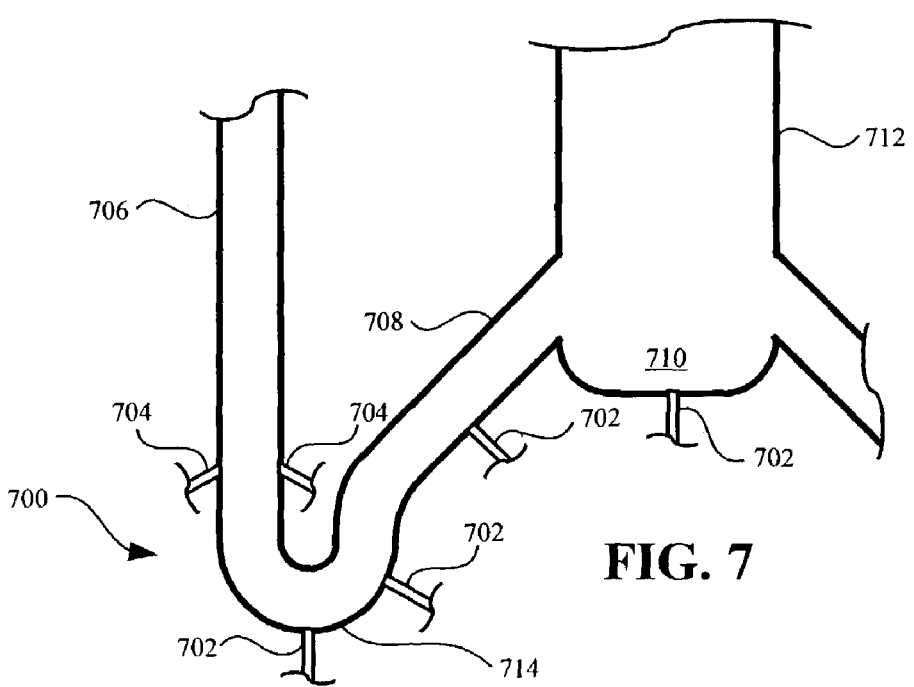
FIG. 7 presents a partial cross sectional view of a "J-Bend" catalyst return system according to another embodiment of the present invention.

FIG. 7 illustrates a "J-Bend" catalyst return system, generally designated by numeral 700, in accordance with another embodiment of the present invention. As shown in FIG. 7, catalyst return 712 is shown in fluid communication with an optional catalyst retention zone 710, which is similar to the catalyst retention zone 134 illustrated in FIG. 1. Catalyst return 712 also is in fluid communication with a plurality of standpipes or arms 708, each of which is provided to transfer catalyst, preferably in a fluidized manner, from the catalyst return 712 and/or catalyst retention zone 710 to the first end of a respective riser reactor 706. More specifically, each of the arms 708 is adapted to deliver catalyst to a U-shaped member 714, which deviates the flow of catalyst from the second end of a respective arm 708 toward the first end of a respective riser reactor 706. Optionally, each of the arms 708 includes a flow control device, not shown, as discussed above with reference to FIG. 1. Preferably, one or more fluidizing agent distributors 702 are provided adjacent to one or more of the catalyst retention zone 710, the arms 708 and the U-shaped member 714, in order to provide a fluidizing agent to maintain the catalyst in a fluidized state. In this embodiment, the oxygenate feedstock preferably is introduced into the sides of the riser reactor 706 through side feedstock introduction nozzles 704. In this manner, the flow of catalyst from the arms to the riser reactors is not restricted by the presence of one or more necks 152, illustrated in FIGS. 1 and 2.

Reverting to FIG. 1, the hydrocarbon conversion apparatus 110 may also include an outlet and outlet line 146 through which the catalyst is removed from the apparatus 110, e.g., for catalyst regeneration. The outlet line 146 is shown as being positioned on the second end 128 of the shell 160 but may be positioned at any position on the apparatus 110. Thus, the hydrocarbon conversion apparatus 110 of the present invention optionally includes an associated catalyst regeneration apparatus, not shown. The catalyst regeneration apparatus is in fluid communication with the hydrocarbon conversion apparatus 110. The catalyst regeneration apparatus includes a catalyst regenerator, which is in fluid communication with the hydrocarbon conversion apparatus 110, and an optional catalyst stripper, not shown, which is in fluid communication with the catalyst regenerator and which is in fluid communication with the hydrocarbon conversion apparatus 110. A first line, shown in part by outlet line 146, provides fluid communication between the catalyst stripper and the outlet on shell 162. A second line, not shown, provides fluid communication between the catalyst stripper and the catalyst regenerator. A third line, shown in part as inlet line 156, provides fluid communication between the catalyst regenerator and the inlet on shell 160. A flow control device, not shown, optionally is positioned on first line to control the flow of catalyst between the shell 160 and the catalyst stripper. Additionally or alternatively, a flow control device, not shown, is positioned on the second line to control the flow of catalyst between the catalyst stripper and the catalyst regenerator. Additionally or alternatively, a flow control device, not shown, is positioned on the third line to control the flow of catalyst between the catalyst regenerator and the shell 160. The flow control devices may be any types of flow control devices currently in use in the art to control catalyst flow through catalyst transfer lines. Useful flow control devices include ball valves, plug valves and slide valves. The catalyst stripper optionally is separate from or integrally formed with the catalyst regenerator. The third line can return catalyst to any portion of the HCA 110. For example, in various embodiments, catalyst is returned to the separation zone 124, as shown in FIG. 1, to the catalyst return 130, the catalyst retention zone 134, the arms 136, directly to riser reactor 114, or any combinations thereof.

The apparatus 110 shown in FIG. 1 functions in the following manner. The apparatus 110 is filled with an appropriate amount of catalyst suitable to carry out the desired hydrocarbon conversion reaction. The catalyst should be of a type that is fluidizable. At least a portion of the catalyst is retained in the catalyst return 130 and the catalyst retention zone 134. The catalyst is fluidized in the catalyst return 130 and the catalyst retention zone 134 by means of a fluidizing agent, which is provided to the hydrocarbon conversion apparatus 110 through the conduits of the fluidizing agent distributors 132. Useful fluidizing agents include, but are not limited to, inert gasses, nitrogen, steam, carbon dioxide, hydrocarbons and air. The choice of fluidizing agent depends upon the type of conversion reaction being conducted in the HCA 110. Desirably the fluidizing agent is unreactive, e.g., inert, in the reaction being conducted in the HCA 110. In other words, it is desirable that the fluidizing agent does not play a part in the hydrocarbon conversion process being conducted in the HCA 110 other than to fluidize the fluidizable catalyst.

Once the catalyst has reached an acceptable fluidized state, a feed is fed into the HCA 110 through feed distributor 154. The feed enters the body of feed distributor 154, passes through the necks 152 of feed distributor 154 and exits through the heads 112 of feed distributor 154. The feed is distributed to each of the riser reactors 114 through their first ends 116. Desirably, the feed is provided in substantially equal streams to each riser reactor 114. By "substantially equal" it is meant that the flow of feed provided to each riser reactor 114 through the feed distributor 154 varies by no more than 25% by volume rate, and varies no more than 25% by mass percent, for each component in the feed, from one riser reactor to another riser reactor. More desirably, the flow of feed provided to each riser reactor 114 through the feed distributor 154 varies by no more than 10% by volume rate, and varies no more than 10% by mass percent for each component in the feed, from one riser reactor to another riser reactor. Most desirably, feed provided to each riser reactor 114 through the feed distributor 154 varies by no more than 1% by volume rate, and varies no more than 1% by mass percent for each component in the feed, from one riser reactor to another riser reactor.

A pressure differential created by the velocity of the feed entering the first ends 116 of the riser reactors 114 and the pressure of the height of fluidizable catalyst in the catalyst return(s) 130 and the catalyst retention zone 134 causes catalyst to be aspirated into the first ends 116 of the riser reactors 114. The catalyst is transported through the riser reactors 114 under well known principles in which the kinetic energy of one fluid, in this case the feed, is used to move another fluid, in this case the fluidized catalyst. The catalyst and feed travel from the first ends 116 to the second ends 118 of the riser reactors 114. As the catalyst and feed travel through the riser reactors 114, the hydrocarbon conversion reaction occurs and a conversion product is produced. The flow of catalyst to the riser reactors 114 are controlled by the flow control devices 144.

By designing the hydrocarbon conversion apparatus 110 with these features, each individual riser reactor 114 operates in a substantially identical manner. With this invention, it is desirable to maintain both the reactant feed rates and the catalyst feed rates at the same rates to each of the riser reactors 114. In this way, the conversion of the feed and selectivity to the desired products will be substantially identical and can run at optimum operational conditions.

The conversion product(s), unreacted feed, if any, and the catalyst exit the riser reactors 114 through their second ends 118 and enter the deviating member 120. The deviating member preferably is a curved pipe, elbow, or other conduit device adapted to receive catalyst, products and unreacted feed, if any, that exits riser reactor 114 through second end 118. The deviating member 120 deviates the flow of the catalyst, products and unreacted feed from the second end of the riser reactor 114 toward inlet 122 on the side wall(s) of separation zone 124. The conversion product(s), unreacted feed, if any, and catalyst then enters the separation zone 124 of shell 160. In the separation zone 124, the conversion product and unreacted feed, if any, are separated from the catalyst by a separation devices 126, such as cyclonic separators, filters, screens, impingement devices, plates, cones, other devices that would separate the catalyst from the product of the conversion reaction, and combinations thereof. Desirably, as shown in FIG. 1, the conversion product and unreacted feed, if any, are separated by a series of cyclonic separators. Once the catalyst has been separated from the conversion product and the unreacted feed, if any, the conversion products and unreacted feed, if any, are removed from the shell 160 through the product exit line 138 for further processing such as separation and purification.

Product exit conduit or conduits 176 from separation device(s) 126 is openly joined to a plenum shell 172. Plenum volume 174 is formed within the boundaries of plenum shell 172 as joined to the section of the shell 160 defining the top of separation zone 124. The plenum shell 172 and plenum volume 174 are provided to collect reaction product and possibly unreacted feedstock exiting separation devices 126 via product exit conduit or conduits 176, and direct that material to product exit line 138. The product exit line 138 is openly joined to separation zone 124 in the vicinity of plenum volume 174, and is provided to convey reaction product and possibly unreacted feedstock away from the apparatus. Such plenum designs are particularly useful in embodiments when a plurality of separation devices are utilized, for example as disclosed in FIGS. 1 and 2. As shown, the product exit conduits 176 from the separation devices 126 are openly joined to the plenum shell 172, and a single, secondary product exit line 138 may be used to carry product away from the hydrocarbon conversion apparatus.

The catalyst, after being separated from the products and unreacted feed, moves from the shell 160 to catalyst return 130 and the catalyst retention zone 134. The catalyst exits shell 160 through the first end 140 of the catalyst return 130 and moves through the catalyst return 130 to the second end 142 of the catalyst returns 130 from which the catalyst moves to the optional catalyst retention zone 134. If desired, the flow of catalyst through the catalyst returns 130 is controlled by the flow control devices 144. If the flow control devices 144 are employed, a height of fluidizable catalyst is maintained above each flow control device 144 in the catalyst return 130 to allow proper function of the flow control device 144.

As discussed above, if necessary or desired, at least a portion of the catalyst is circulated to the catalyst regeneration apparatus. Catalyst to be regenerated is removed from the shell 160 through the outlet and outlet line 146 and transported, if desired, to the catalyst stripper. Optionally, the flow of catalyst between the hydrocarbon conversion apparatus 110 and the catalyst stripper is controlled by a flow control device, not shown. In the catalyst stripper, the catalyst is stripped of most of readily removable organic materials (organics). Stripping procedures and conditions for individual hydrocarbon conversion processes are within the skill of a person of skill in the art. The stripped catalyst is transferred from the catalyst stripper to the catalyst regenerator through a second line, not shown. The flow of catalyst through the second line optionally is controlled by one or more flow control devices. In the catalyst regenerator, carbonaceous deposits formed on the catalyst during a hydrocarbon conversion reaction are at least partially removed from the catalyst. The regenerated catalyst is then transferred to the shell 160 of the hydrocarbon conversion apparatus 110 through a third line. The flow of catalyst through the third line optionally is controlled by one or more flow control device. A transport gas is typically provided to the third line to facilitate transfer of the catalyst from the catalyst regenerator to the hydrocarbon conversion apparatus 110. The catalyst is returned to the shell 160 through the inlet 156.

FIG. 2 illustrates a hydrocarbon conversion apparatus similar to the one shown in FIG. 1 having a quiescent zone 204 to facilitate catalyst removal. In this embodiment, the catalyst return 130 includes a wall extension 202, which extends upwardly into the second end 128 of shell 160, and a funnel portion 208. The wall extension 202 and the funnel portion 208 define a quiescent zone 204 in which a portion of the catalyst is retained prior to being removed from the shell 160 via outlet 146. As catalyst accumulates in the quiescent zone 204 up to the edge of wall extension 202, excess catalyst will spill out of the quiescent zone 204 and into catalyst return 130.

FIG. 2 also illustrates an embodiment of the present invention wherein the first ends 168 of arms 136 act as the catalyst retention zone. In this embodiment, the plurality of arms 136 optionally meet at an apex 206 rather than meeting in a separate and distinct catalyst retention zone 134, illustrated in FIG. 1. In the embodiment shown in FIG. 2, catalyst flow to the riser reactors 114 is controlled by flow control devices 144, discussed above. An apex fluidizing agent distributor 210 optionally is provided adjacent the apex 206 to facilitate catalyst flow into arms 136, as shown in FIG. 2.

It will be appreciated that the HCA of FIG. 2 operates in a similar manner to the HCA described above with regard to FIG. 1.

Figure 3A:
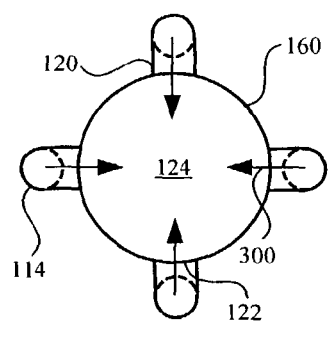
FIGS. 3A–3C present partial cross sectional top views of three embodiments of hydrocarbon conversion apparatuses according to the present invention.
Figure 3B:
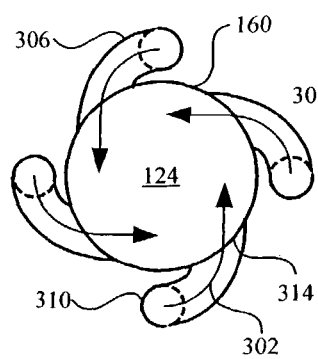
Figure 3C:
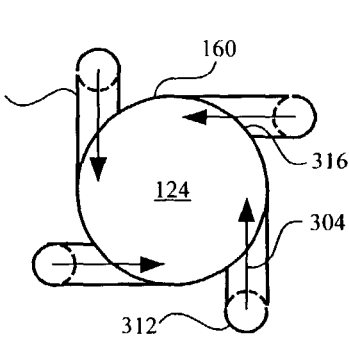

Representative embodiments of possible configurations of riser reactors and separation zones in accordance with the present invention are shown by top views in FIGS. 3A–3C. Although each of FIGS. 3A–3C illustrates an HCA 110 having four riser reactors 114, it is, to be understood that these configurations could be modified to provide 2, 3, 4, 5, 6 or even more than 6 riser reactors similarly oriented about separation zone 124.

FIG. 3A shows a possible configuration for the riser reactors 114 for the HCA 110 shown in FIG. 1. As shown in FIG. 3A, the riser reactors 114 are oriented externally and adjacent to separation zone 124 defined by shell 160. Each riser reactor 114 is coupled to a deviating member 120, which is adapted to deviate the flow of catalyst, product and unreacted feed, if any, from the top of riser reactors 114 toward an inlet 122 on the side wall of the shell 160 defining the separation zone 124. Each of the deviating members 120 deviates the flow of catalyst, product and unreacted feed, if any, from the top of the riser reactors 114 toward the separation zone 124, preferably toward the center axis 166 (or centroid line), as shown in FIG. 1, of the separation zone 124. Optionally, each deviating member is a tubular member arcuously curved about a single plane, which preferably passes through the center axis 166 (or centroid line) of the separation zone 124 and the center axis 158 (or centroid line) of the riser reactor 114, as shown in FIG. 1. The flow of material from the top of the riser reactors 114 is illustrated by arrow 300, which preferably is oriented perpendicular to an imaginary tangent line on the cylindrical outer surface of the shell 160 defining separation zone 124 adjacent the center of the inlet 122. If the shell and separation zone are not oriented in a cylinder, the flow of material is preferably oriented substantially perpendicular to the surface of the shell 160 adjacent inlet 122. In this embodiment, the catalyst, product and any unreacted feed from riser reactors on opposite sides of the separation zone 124 may collide with each other, or more likely with separation devices 126, shown in FIG. 1, thereby facilitating mixing of these components and providing increased reaction time for the hydrocarbon conversion reaction, which may continue to occur inside the separation zone 124.

FIG. 3B shows another embodiment of the present invention wherein separation of the products of the hydrocarbon conversion reaction from the catalyst is facilitated by the formation of a cyclone within the separation zone. In this embodiment, the cyclone is formed by the flow of material entering the separation zone at relatively high superficial gas velocities from the riser reactors via arcuous deviating members. As shown in FIG. 3B, the riser reactors 310 are oriented externally and adjacent to separation zone 124 defined by shell 160. Each riser reactor 310 is coupled to an arcuous deviating member 306, which is adapted to deviate the flow of catalyst, product and unreacted feed, if any, from the top of riser reactors 310 toward the separation zone 124. Optionally, each deviating member 306 is a tubular member arcuously curved about a plurality of planes. The flow of material from the top of the riser reactors 310 is illustrated by arrow 302, which preferably is oriented at an oblique angle, e.g., not perpendicular, to an imaginary tangent line on the cylindrical outer surface of the shell 160 defining separation zone 124 at the inlet 314. Accordingly, each inlet 314 is offset from its respective riser reactor 310. Each of the arcuous deviating members 306 deviates the flow of catalyst, product and unreacted feed, if any, illustrated by arrow 302, from the top of the riser reactors 310 toward a peripheral region of the separation zone 124 via inlet 314. "Peripheral region" means a region of the separation zone 124 other than the region defined by the center axis 166, shown in FIG. 1, or central region thereof. Preferably, each arcuous deviating member 306 directs the flow from its respective riser reactor 310 to a similarly situated respective peripheral region of the separation zone. By directing the catalyst, product and unreacted feed to similarly situated respective peripheral regions of the reactor, a cyclone is formed within the separation zone 124. The formation of a cyclone facilitates catalyst separation in a manner similar to conventional cyclone separation units, illustrated as separation devices 126 in FIGS. 1 and 2. By forming a cyclone within the separation zone, the number of separation devices 126 within the separation zone 124 may be advantageously reduced while maintaining similar or better catalyst separation over conventional HCA's.

FIG. 3C shows another embodiment of the present invention wherein separation of the products of the hydrocarbon conversion reaction from the catalyst is facilitated, as with FIG. 3B, by the formation of a cyclone within the separation unit. The cyclone is formed by the flow of material entering the separation zone 124 at relatively high superficial gas velocities from the riser reactors via deviating members 308. As shown in FIG. 3C, the riser reactors 312 are oriented externally and adjacent to separation zone 124 defined by shell 160. Additionally, the riser reactors 312 are offset to a side of the reactor relative to the embodiments illustrated in FIGS. 3A and 3B. Each riser reactor 312 is coupled to a deviating member 308, which is adapted to deviate the flow of catalyst, product and unreacted feed, if any, from the top of riser reactors 312 toward the separation zone 124. Optionally, each deviating member 308 is a tubular member curved about a single plane, which is preferably parallel to a second plane passing through the axis of the separation zone 124. The flow of material from the top of the riser reactors 312 is illustrated by arrow 304, which preferably is oriented at an oblique angle, e.g., not perpendicular, to an imaginary tangent line on the cylindrical outer surface of the shell 160 defining separation zone 124 at inlet 316. Each of the deviating members 308 deviates the flow of catalyst, product and unreacted feed, if any, illustrated by arrow 304, from the top of the riser reactors 312 toward a peripheral region of the separation zone 124. Preferably, each deviating member directs the flow from its respective riser reactor 312 to a similarly situated respective peripheral region of the separation zone 124. By directing the catalyst, product and unreacted feed to similarly situated respective peripheral regions of the reactor, a cyclone is formed within the separation zone 124.

Figure 4:
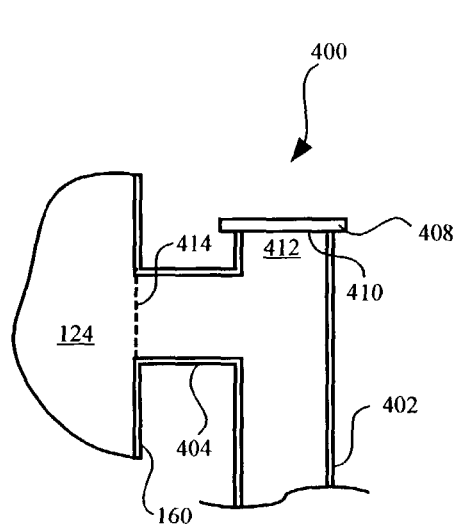
FIG. 4 presents a cut-away side view of an elbow deviating member according to one embodiment of the present invention.

Although FIGS. 1–3 illustrate HCA's having deviating members formed of tubular members, one or more of the deviating members can also be formed as an elbow, as illustrated in FIG. 4. In this embodiment, each riser reactor 402 is in fluid communication with an elbow deviating member, generally designated 400, which includes a contacting plate 408, a catalyst contact region 412 and a delivery member 404. After catalyst, product and unreacted feedstock, if any, has traveled up the riser reactor 402 it enters catalyst contact region 412. Some catalyst collides at relatively high gas superficial velocities with the inner surface 410 of contacting plate 408. Ideally, the gas superficial velocity is high enough so that an amount of catalyst is temporarily retained in catalyst contact region 412. As more catalyst flows up riser reactor 402, the catalyst contacts the retained catalyst in the catalyst contact region 412, and is deviated thereby into delivery member 404. Delivery member 404 is adapted to receive catalyst, product and unreacted feedstock, if any, from the catalyst contact region 412 and direct the catalyst, product and unreacted feedstock toward the inlet 414 formed in shell 160. The delivery member 404 optionally is formed of a pipe or tubular member, or any other suitable shape for delivering catalyst, product and unreacted feed, if any, from the catalyst contact region 412 to inlet 414. By contacting retained catalyst particles in the catalyst contact region 412, rather than contacting a wall of the deviating member, erosion in the deviating member 400 is advantageously minimized. The angle formed by the center axis of riser reactor 402 and the axis of delivery member 404 is preferably about 90 degrees, although other angles are possible.

As shown in FIGS. 1 and 2, the deviating member 120 directs the catalyst, product and unreacted feed, if any from the riser reactor 114 to an inlet 122 in the side wall of the shell 160 defining separation zone 124. That is, the catalyst, product and unreacted feed are introduced directly into the separation zone 124. A first portion of the catalyst, product and unreacted feed stock enters an inlet in one or more of the separation devices 126 wherein the catalyst and product are separated, e.g., by centrifugation. A second portion of the catalyst falls to catalyst return 130 without being processed by the separation devices 126.

Figure 5:
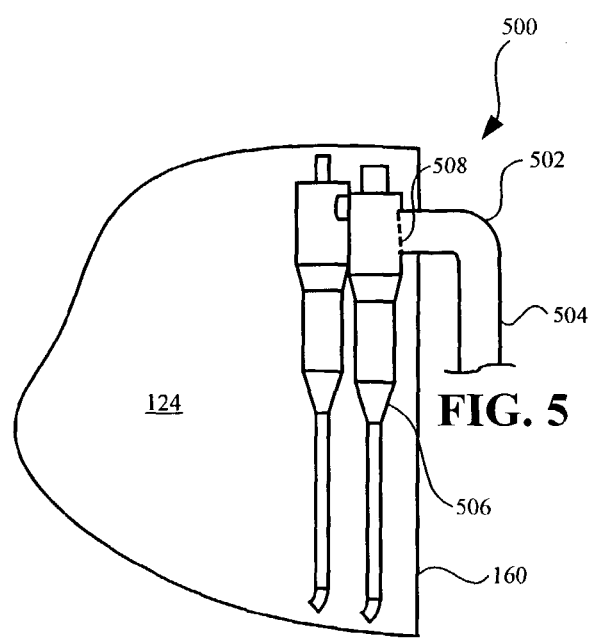
FIG. 5 presents a cut-away partial cross sectional side view of a riser reactor closed-coupled with a cyclone separator.

FIG. 5 illustrates another embodiment of the present invention, generally designated by numeral 500, wherein all of the material from the deviating member is sent directly to one or more separation devices 506 thereby ensuring efficient separation of catalyst from product of the hydrocarbon conversion reaction. That is, one or more riser reactors 504 are closely-coupled with a separation device 508 within, or without, separation zone 124. As shown in FIG. 5, riser reactor 504 is in fluid communication with a deviating member 502, which directs catalyst, product and unreacted feed, if any, through shell 160, which defines separation zone 124. However, unlike the previously-described embodiments, the deviating member 502 optionally extends inside the separation zone 124 and directs the catalyst, product and unreacted feed, if any, to inlet 508 on separation device 506. Although FIG. 5 illustrates the deviating member 502 in fluid communication with two cyclonic separators in series, any of the types of catalyst separators described above may be implemented in this embodiment. In the separation device 506, catalyst is efficiently separated from the product of the hydrocarbon conversion reaction. Optionally, each respective riser reactor and deviating member combination is equipped with its own separation device. Alternatively, a plurality of deviating members from a plurality of associated riser reactors can direct catalyst, product and unreacted feedstock, if any, to a single separation device. Optionally, because the riser reactor of this embodiment is closely-coupled with one or more separation devices, the separation device may be external to separation zone 124. If the separation device is external to the separation zone, then a separation zone may be advantageously reduced in size. Additionally, more cyclones may be incorporated in the present invention if they are oriented externally to the separation zone, without having to enlarge the size of the separation zone.

While the riser reactors and catalyst returns are shown in the various Figures as having a circular cross section, the riser reactors and catalyst returns may have any cross section, which would facilitate operation of the hydrocarbon conversion apparatus. Other useful cross sections for the riser reactors and the catalyst returns include elliptical cross sections, polygonal cross sections and cross sections of sections of ellipses and polygons. Desirable cross-sections for the riser reactors and catalyst returns include circles and regular polygons with sides of equal lengths. By "regular", it is meant that the shape of the cross-section has no line segments with vertices, inside the boundaries of the shape, having angles greater than 180°. The most desirable cross-sections are circles, and triangles, squares, and hexagons with sides of equal length. The means of determining cross-sectional areas for any cross-section shape is based on long established geometric principles well known to those skilled in the art. Similarly, desirable cross-sections for the separation zone include circles and regular polygons with sides of equal lengths. The most desirable cross-sections are circles, and triangles, squares, and hexagons with sides of equal length.

While the position of the riser reactors relative to the separation zone are shown in the figures as equidistant and symmetrical, alternate configurations are within the scope of the present invention. For example, the riser reactors may be positioned on one side of the separation zone in a hemispherical layout. As another example, when the separation zone has a circular or approximately circular cross-section, the riser reactors may be positioned in a line along the diameter the separation zone. One skilled in the art will appreciate that a wide variety of configurations of the risers relative to the separation zone may be utilized in the present invention.

The hydrocarbon conversion apparatus of the present invention is useful to conduct most any hydrocarbon conversion process in which a fluidized catalyst is employed. Typical reactions include, for example, olefin interconversion reactions, oxygenate to olefin conversion reactions, oxygenate to gasoline conversion reactions, malaeic anhydride formulation, vapor phase methanol synthesis, phthalic anhydride formulation, Fischer Tropsch reactions, and acrylonitrile formulation.

The hydrocarbon conversion apparatus of the present invention is particularly suited for conducting an oxygenate to olefin conversion reaction. In an oxygenate to olefin conversion reaction, an oxygenate is converted to an olefin by contacting an oxygenate feed with a catalyst under conditions sufficient to convert the oxygenate to an olefin.

The process for converting oxygenates to light olefins employs a feed including an oxygenate. As used herein, the term "oxygenate" is defined to include, but is not necessarily limited to, hydrocarbons containing oxygen such as the following: aliphatic alcohols, ethers, carbonyl compounds (aldehydes, ketones, carboxylic acids, carbonates, and the like), and mixtures thereof. The aliphatic moiety desirably should contain in the range of from about 1–10 carbon atoms and more desirably in the range of from about 1–4 carbon atoms. Representative oxygenates include, but are not necessarily limited to, lower molecular weight straight chain or branched aliphatic alcohols, and their unsaturated counterparts. Examples of suitable oxygenates include, but are not necessarily limited to the following: methanol; ethanol; n-propanol; isopropanol; $C_4$–$C_{10}$ alcohols; methyl ethyl ether; dimethyl ether; diethyl ether; di-isopropyl ether; methyl formate; formaldehyde; di-methyl carbonate; methyl ethyl carbonate; acetone; and mixtures thereof. Desirably, the oxygenate used in the conversion reaction is selected from the group consisting of methanol, dimethyl ether and mixtures thereof. More desirably the oxygenate is methanol. The total charge of feed to the riser reactors may contain additional components, such as diluents.

One or more diluents may be fed to the riser reactors with the oxygenates, such that the total feed mixture comprises diluent in a range of from about 1 mol % and about 99 mol %. Diluents that may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Desired diluents include, but are not necessarily limited to, water and nitrogen.

A portion of the feed may be provided to the reactor in liquid form. When a portion of the feed is provided in a liquid form, the liquid portion of the feed may be either oxygenate, diluent or a mixture of both. The liquid portion of the feed may be directly injected into the individual riser reactors, or entrained or otherwise carried into the riser reactors with the vapor portion of the feed or a suitable carrier gas/diluent. By providing a portion of the feed (oxygenate and/or diluent) in the liquid phase, the temperature in the riser reactors is controllable. The exothermic heat of reaction of oxygenate conversion is partially absorbed by the endothermic heat of vaporization of the liquid portion of the feed. Controlling the proportion of liquid feed to vapor feed fed to the reactor is one possible process for controlling the temperature in the reactor and in particular in the riser reactors.

The amount of feed provided in a liquid form, whether fed separately or jointly with the vapor feed, is from about 0.1 wt. % to about 85 wt. % of the total oxygenate content plus diluent in the feed. More desirably, the range is from about 1 wt. % to about 75 wt. % of the total oxygenate plus diluent feed, and most desirably the range is from about 5 wt. % to about 65 wt. %. The liquid and vapor portions of the feed may be the same composition, or may contain varying proportions of the same or different oxygenates and same or different diluents. One particularly effective liquid diluent is water, due to its relatively high heat of vaporization, which allows for a high impact on the reactor temperature differential with a relatively small rate. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the feed may be split into portions and introduced to riser reactors a multiplicity of locations along the length of the riser reactors. This may be done with either the oxygenate feed, the diluent or both. Typically, this is done with the diluent portion of the feed. Another option is to provide a nozzle, which introduces the total liquid fraction of the feed to the riser reactors in a manner such that the nozzle forms liquid droplets of an appropriate size distribution, which, when entrained with the gas and solids introduced to the riser reactors, vaporize gradually along the length of the riser reactors. Either of these arrangements or a combination thereof may be used to better control the temperature differential in the riser reactors. The means of introducing a multiplicity of liquid feed points in a reactor or designing a liquid feed nozzle to control droplet size distribution is well known in the art and is not discussed here.

The catalyst suitable for catalyzing an oxygenate-to-olefin conversion reaction includes a molecular sieve and mixtures of molecular sieves. Molecular sieves may be zeolitic (zeolites) or non-zeolitic (non-zeolites). Useful catalysts may also be formed from mixtures of zeolitic and non-zeolitic molecular sieves. Desirably, the catalyst includes a non-zeolitic molecular sieve. Desired molecular sieves for use with an oxygenate to olefins conversion reaction include "small" and "medium" pore molecular sieves. "Small pore" molecular sieves are defined as molecular sieves with pores having a diameter of less than about 5.0 Angstroms. "Medium pore" molecular sieves are defined as molecular sieves with pores having a diameter from about 5.0 to about 10.0 Angstroms.

Useful zeolitic molecular sieves include, but are not limited to, mordenite, chabazite, erionite, ZSM-5, ZSM-34, ZSM-48 and mixtures thereof. Methods of making these molecular sieves are known in the art and need not be discussed here. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof.

Silicoaluminophosphates ("SAPOs") are one group of non-zeolitic molecular sieves that are useful in an oxygenate to olefins conversion reaction. SAPOs comprise a three-dimensional microporous crystal framework structure of [$SiO_2$], [$AlO_2$] and [$PO_2$] tetrahedral units. The way Si is incorporated into the structure is determined by $^{29}Si$ MAS NMR. See Blackwell and Patton, J. Phys. Chem., 92, 3965 (1988). The desired SAPO molecular sieves will exhibit one or more peaks in the $^{29}Si$ MAS NMR, with a chemical shift (Si)] in the range of –88 to –96 ppm and with a combined peak area in that range of at least 20% of the total peak area of all peaks with a chemical shift (Si)] in the range of –88 ppm to –115 ppm, where the (Si)] chemical shifts refer to external tetramethylsilane (TMS).

It is desired that the silicoaluminophosphate molecular sieve used in such a process have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $SiAl_2$ ratio of not greater than 0.32 being particularly preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing [$SiO_2$], [$AlO_2$], and [$PO_2$] tetrahedral units. This type of framework is effective in converting various oxygenates into olefin products.

Suitable silicoaluminophosphate molecular sieves for use in an oxygenate to olefin conversion process include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

Additional olefin-forming molecular sieve materials may be mixed with the silicoaluminophosphate catalyst if desired. Several types of molecular sieves exist, each of which exhibit different properties. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. Preferred molecular sieves that may be combined with a silicoaluminophosphate catalyst include ZSM-5, ZSM-34, erionite, and chabazite.

Substituted SAPOs form a class of molecular sieves known as "MeAPSOs," which are also useful in the present invention. Processes for making MeAPSOs are known in the art. SAPOs with substituents, such as MeAPSOs, also may be suitable for use in the present invention. Suitable substituents, "Me," include, but are not necessarily limited to, nickel, cobalt, manganese, zinc, titanium, strontium, magnesium, barium, and calcium. The substituents may be incorporated during synthesis of the MeAPSOs. Alternately, the substituents may be incorporated after synthesis of SAPOs or MeAPSOs using many methods. These methods include, but are not necessarily limited to, ion-exchange, incipient wetness, dry mixing, wet mixing, mechanical mixing, and combinations thereof.

Desired MeAPSOs are small pore MeAPSOs having pore size smaller than about 5 Angstroms. Small pore MeAPSOs include, but are not necessarily limited to, NiSAPO-34, CoSAPO-34, NiSAPO-17, CoSAPO-17, and mixtures thereof.

Aluminophosphates (ALPOs) with substituents, also known as "MeAPOs," are another group of molecular sieves that may be suitable for use in an oxygenate to olefin conversion reaction, with desired MeAPOs being small pore MeAPOs. Processes for making MeAPOs are known in the art. Suitable substituents include, but are not necessarily limited to, nickel, cobalt, manganese, zinc, titanium, strontium, magnesium, barium, and calcium. The substituents may be incorporated during synthesis of the MeAPOs. Alternately, the substituents may be incorporated after synthesis of ALPOs or MeAPOs using many methods. The methods include, but are not necessarily limited to, ion-exchange, incipient wetness, dry mixing, wet mixing, mechanical mixing, and combinations thereof.

The molecular sieve may also be incorporated into a solid composition, preferably solid particles, in which the molecular sieve is present in an amount effective to catalyze the desired conversion reaction. The solid particles may include a catalytically effective amount of the molecular sieve and matrix material, preferably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. Such matrix, e.g., filler and binder, materials include, for example, synthetic and naturally occurring substances, metal oxides, clays, silicas, aluminas, silica-aluminas, silica-magnesias, silica-zirconias, silica-thorias, silica-beryllias, silica-titanias, silica-alumina-thorias, silica-aluminazirconias, and mixtures of these materials.

The solid catalyst composition preferably comprises about 1% to about 99%, more preferably about 5% to about 90%, and still more preferably about 10% to about 80%, by weight of molecular sieve; and an amount of about 1% to about 99%, more preferably about 5% to about 90%, and still more preferably about 10% to about 80%, by weight of matrix material.

The preparation of solid catalyst compositions, e.g., solid particles, comprising the molecular sieve and matrix material, is conventional and well known in the art and, therefore, is not discussed in detail here.

The catalyst may further contain binders, fillers, or other material to provide better catalytic performance, attrition resistance, regenerability, and other desired properties. Desirably, the catalyst is fluidizable under the reaction conditions. The catalyst should have particle sizes of from about 20μ to about 3,000μ, desirably from about 30μ to about 200μ, and more desirably from about 50μ to about 150μ. The catalyst may be subjected to a variety of treatments to achieve the desired physical and chemical characteristics. Such treatments include, but are not necessarily limited to, calcination, ball milling, milling, grinding, spray drying, hydrothermal treatment, acid treatment, base treatment, and combinations thereof.

Desirably, in an oxygenate to olefin conversion reaction conducted in the hydrocarbon conversion apparatus of the present invention employs a gas superficial velocity in the riser reactors of greater than 1 meter per second (m/s). As used herein and in the claims, the term, "gas superficial velocity," is defined as the volumetric flow rate of vaporized feedstock, and any diluent, divided by the reactor cross-sectional area. Because the oxygenate is converted to a product including a light olefin while flowing through the reactor, the gas superficial velocity may vary at different locations within the reactor depending on the total number of moles of gas present and the cross section of a particular location in the reactor, temperature, pressure, and other relevant reaction parameters. The gas superficial velocity, including any diluents present in the feedstock, is maintained at a rate greater than 1 meter per second (m/s) at any point in the reactor. Desirably, the gas superficial velocity is greater than about 2 m/s. More desirably, the gas superficial velocity is greater than about 2.5 m/s. Even more desirably, the gas superficial velocity is greater than about 4 m/s. Most desirably, the gas superficial velocity is greater than about 8 m/s.

Maintaining the gas superficial velocity at these rates increases the approach to plug flow behavior of the gases flowing in the riser reactors. As the gas superficial velocity increases above 1 m/s, a reduction in axial diffusion or back mixing of the gases results from a reduction in internal recirculation of solids, which carry gas with them. (Ideal plug flow behavior occurs when elements of the homogeneous fluid reactant move through a reactor as plugs moving parallel to the reactor axis). Minimizing the back mixing of the gases in the reactor increases the selectivity to the desired light olefins in the oxygenate conversion reaction.

When the gas superficial velocity approaches 1 m/s or higher, a substantial portion of the catalyst in the reactor may be entrained with the gas exiting the riser reactors. At least a portion of the catalyst exiting the riser reactors is recirculated to recontact the feed through the catalyst return.

Desirably, the rate of catalyst, comprising molecular sieve and any other materials such as binders, fillers, etc., recirculated to recontact the feed is from about 1 to about 100 times, more desirably from about 10 to about 80 times, and most desirably from about 10 to about 50 times the total feed rate, by weight, of oxygenates to the reactor.

The temperature useful to convert oxygenates to light olefins varies over a wide range depending, at least in part, on the catalyst, the fraction of regenerated catalyst in a catalyst mixture, and the configuration of the reactor apparatus and the reactor. Although these processes are not limited to a particular temperature, best results are obtained if the process is conducted at a temperature from about 200° C. to about 700° C., desirably from about 250° C. to about 600° C., and most desirably from about 300° C. to about 500° C. Lower temperatures generally result in lower rates of reaction, and the formation rate of the desired light olefin products may become markedly slower. However, at temperatures greater than 700° C., the process may not form an optimum amount of light olefin products, and the rate at which coke and light saturates form on the catalyst may become too high.

Light olefins will form—although not necessarily in optimum amounts—at a wide range of pressures including, but not limited to, pressures from about 0.1 kPa to about 5 MPa. A desired pressure is from about 5 kPa to about 1 MPa and most desirably from about 20 kPa to about 500 kPa. The foregoing pressures do not include that of a diluent, if any, and refer to the partial pressure of the feed as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins will still form and, for that reason, these extremes of pressure are considered part of the present invention.

A wide range of WHSV's for the oxygenate conversion reaction, defined as weight of total oxygenate fed to the riser reactors per hour per weight of molecular sieve in the catalyst in the riser reactors, function with the present invention. The total oxygenate fed to the riser reactors includes all oxygenate in both the vapor and liquid phase. Although the catalyst may contain other materials, which act as inerts, fillers or binders, the WHSV is calculated using only the weight of molecular sieve in the catalyst in the riser reactors. The WHSV is desirably high enough to maintain the catalyst in a fluidized state under the reaction conditions and within the reactor configuration and design. Generally, the WHSV is from about 1 $hr^{-1}$ to about 5000 $hr^{-1}$, desirably from about 2 $hr^{-1}$ to about 3000 $hr^{-1}$, and most desirably from about 5 $hr^{-1}$ to about 1500 $hr^{-1}$. The applicants have discovered that operation of the oxygenate to olefin conversion reaction at a WHSV greater than 20 $hr^{-1}$ reduces the methane content in the product slate of the conversion reaction. Thus, the conversion reaction is desirably operated at a WHSV of at least about 20 $hr^{-1}$. For a feed comprising methanol, dimethyl ether, or mixtures thereof, the WHSV is desirably at least about 20 $hr^{-1}$ and more desirably from about 20 $hr^{-1}$ to about 300 $hr^{-1}$.

It is particularly preferred that the reaction conditions for making olefins from an oxygenate comprise a WHSV of at least about 20 $hr^{-1}$ and a Temperature Corrected Normalized Methane Selectivity (TCNMS) of less than about 0.016. As used herein, TCNMS is defined as the Normalized Methane Selectivity (NMS) when the temperature is less than 400° C. The NMS is defined as the methane product yield divided by the ethylene product yield wherein each yield is measured on or is converted to a weight % basis. When the temperature is 400° C. or greater, the TCNMS is defined by the following equation, in which T is the average temperature within the reactor in ° C.:

$$TCNMS = \frac{NMS}{1+(((T-400)/400)\times 14.84)}.$$

Oxygenate conversion should be maintained sufficiently high to avoid the need for commercially unacceptable levels of feed recycling. While 100% oxygenate conversion is desired for the purpose of completely avoiding feed recycle, a reduction in unwanted by-products is observed frequently when the conversion is about 98% or less. Since recycling up to as much as about 50% of the feed is commercially acceptable, conversion rates from about 50% to about 98% are desired. Conversion rates may be maintained in this range—50% to about 98%—using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst recirculation rate; reactor apparatus configuration; reactor configuration; feed composition; amount of liquid feed relative to vapor feed (as will be discussed below); amount of recirculated catalyst; degree of catalyst regeneration; and other parameters, which affect the conversion.

During the conversion of oxygenates to light olefins, carbonaceous deposits accumulate on the catalyst used to promote the conversion reaction. At some point, the build up of these carbonaceous deposits causes a reduction in the capability of the catalyst to convert the oxygenate feed to light olefins. At this point, the catalyst is partially deactivated. When a catalyst can no longer convert an oxygenate to an olefin product, the catalyst is considered to be fully deactivated. As an optional step in an oxygenate to olefin conversion reaction, a portion of the catalyst is withdrawn from the reactor and at least a portion of the portion removed from the reactor is partially, if not fully, regenerated in a regeneration apparatus, such as regeneration apparatus 80 as shown in FIG. 4. By regeneration, it is meant that the carbonaceous deposits are at least partially removed from the catalyst. Desirably, the portion of the catalyst withdrawn from the reactor is at least partially deactivated. The remaining portion of the catalyst in the reactor is re-circulated without regeneration, as described above. The regenerated catalyst, with or without cooling, is then returned to the reactor. Desirably, the rate of withdrawing the portion of the catalyst for regeneration is from about 0.1% to about 99% of the rate of the catalyst exiting the reactor. More desirably, the rate is from about 0.2% to about 50%, and, most desirably, from about 0.5% to about 5%.

Desirably, a portion of the catalyst, comprising molecular sieve and any other materials such as binders, fillers, etc., is removed from the reactor for regeneration and recirculation back to the reactor at a rate of from about 0.1 times to about 10 times, more desirably from about 0.2 to about 5 times, and most desirably from about 0.3 to about 3 times the total feed rate of oxygenates to the reactor. These rates pertain to the catalyst containing molecular sieve only, and do not include non-reactive solids. The rate of total solids, i.e., catalyst and non-reactive solids, removed from the reactor for regeneration and recirculation back to the reactor will vary these rates in direct proportion to the content of non-reactive solids in the total solids.

Desirably, the catalyst regeneration is carried out in a regeneration apparatus in the presence of a gas comprising oxygen or other oxidants. Examples of other oxidants include, but are not necessarily limited to, singlet $O_2$, $O_3$, $SO_3$, $N_2O$, NO, $NO_2$, $N_2O_5$, and mixtures thereof. Air and air diluted with nitrogen or $CO_2$ are desired regeneration gases. The oxygen concentration in air may be reduced to a controlled level to minimize overheating of, or creating hot spots in, the regenerator. The catalyst may also be regenerated reductively with hydrogen, mixtures of hydrogen and carbon monoxide, or other suitable reducing gases.

The catalyst may be regenerated in any number of methods—batch, continuous, semi-continuous, or a combination thereof. Continuous catalyst regeneration is a desired method. Desirably, the catalyst is regenerated to a level of remaining coke from about 0.01 wt % to about 15 wt % of the weight of the catalyst.

The catalyst regeneration temperature should be from about 250° C. to about 750° C., and desirably from about 500° C. to about 700° C. Because the regeneration reaction takes place at a temperature considerably higher than the oxygenate conversion reaction, it may be desirable to cool at least a portion of the regenerated catalyst to a lower temperature before it is sent back to the reactor. A heat exchanger, not shown, located external to the regeneration apparatus may be used to remove some heat from the catalyst after it has been withdrawn from the regeneration apparatus. When the regenerated catalyst is cooled, it is desirable to cool it to a temperature, which is from about 200° C. higher to about 200° C. lower than the temperature of the catalyst withdrawn from the reactor. More desirably, the regenerated catalyst is cooled to a temperature from about 10° C. to about 200° C. lower than the temperature of the catalyst withdrawn from the reactor. This cooled catalyst then may be returned to either some portion of the reactor, the regeneration apparatus, or both. When the regenerated catalyst from the regeneration apparatus is returned to the reactor, it may be returned to any portion of the reactor. It may be returned to the catalyst containment area to await contact with the feed, the separation zone to contact products of the feed or a combination of both.

Desirably, catalyst regeneration is carried out at least partially deactivated catalyst that has been stripped of most of readily removable organic materials (organics) in a stripper or stripping chamber first. This stripping is achieved by passing a stripping gas over the spent catalyst at an elevated temperature. Gases suitable for stripping include steam, nitrogen, helium, argon, methane, $CO_2$, CO, hydrogen, and mixtures thereof. A preferred gas is steam. Gas hourly space velocity (GHSV, based on volume of gas to volume of catalyst and coke) of the stripping gas is from about 0.1 $h^{-1}$ to about 20,000 $h^{-1}$. Acceptable temperatures of stripping are from about 250° C. to about 750° C., and desirably from about 350° C. to about 675° C.

The process of making the preferred olefin product in this invention can include the additional step of making the oxygenate compositions from hydrocarbons such as oil, coal, tar sand, shale, biomass and natural gas. Processes for making the compositions are known in the art. These processes include fermentation to alcohol or ether, making synthesis gas, then converting the synthesis gas to alcohol or ether. Synthesis gas is produced by known processes such as steam reforming, autothermal reforming and partial oxidization.

One skilled in the art will also appreciate that the olefins produced by the oxygenate-to-olefin conversion reaction of the present invention optionally are polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these processes involve contacting the olefin product with a polyolefin-forming catalyst at a pressure and temperature effective to form the polyolefin product.

A preferred polyolefin-forming catalyst is a metallocene catalyst. The preferred temperature range of operation is between 50° C. and 240° C. and the reaction is carried out at low, medium or high pressure, being anywhere from 1 bar to 200 bars. For processes carried out in solution, an inert diluent optionally is used, and the preferred operating pressure range is between 10 and 150 bars, with a preferred temperature between 120° C. and 230° C. For gas phase processes, it is preferred that the temperature generally be from 60° C. to 160° C., and that the operating pressure be from 5 bars to 50 bars.

In addition to polyolefins, numerous other olefin derivatives may be formed from the olefins produced by the process of the present invention or olefins recovered therefrom. These include, but are not limited to, aldehydes, alcohols, acetic acid, linear alpha olefins, vinyl acetate, ethylene dichloride and vinyl chloride, ethylbenzene, ethylene oxide, ethylene glycol, cumene, isopropyl alcohol, acrolein, allyl chloride, propylene oxide, acrylic acid, ethylene-propylene rubbers, and acrylonitrile, and trimers and dimers of ethylene, propylene or butylenes. The processes of manufacturing these derivatives are well known in the art, and therefore are not discussed here.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A hydrocarbon conversion apparatus, comprising:
   (a) a plurality of riser reactors, each having a first end into which a catalyst can be fed, and a second end through which the catalyst can exit;
   (b) a separation zone having a plurality of inlets, the separation zone being provided to separate the catalyst from products of a reaction conducted in the hydrocarbon conversion apparatus;
   (c) a plurality of deviating members, each deviating member being a curved pipe, elbow or conduit device attached to the second end of a riser reactor so as to receive catalyst, products and unreacted feed and deviate flow of the catalyst, products and unreacted feed toward a respective inlet of the separation zone, wherein each of the plurality of riser reactors includes a center axis extending between the first and second ends thereof, and wherein the plurality of inlets are not oriented along the center axes of the riser reactors;
   (d) a catalyst retention zone provided to contain catalyst, which can be fed to the riser reactors; and
   (e) a catalyst return in fluid communication between the separation zone and the catalyst retention zone.

2. The hydrocarbon conversion apparatus of claim 1, wherein the apparatus further comprises:
   (f) a plurality of arms, each arm in fluid communication between the catalyst retention zone and the first end of a respective riser reactor.

3. The hydrocarbon conversion apparatus of claim 1, wherein the apparatus further comprises:
   (f) a feed distributor including a plurality of feed heads positioned adjacent to the first ends of the riser reactors.

4. The hydrocarbon conversion apparatus of claim 1, wherein the hydrocarbon conversion apparatus includes two riser reactors.

5. The hydrocarbon conversion apparatus of claim 1, wherein the hydrocarbon conversion apparatus includes three riser reactors.

6. The hydrocarbon conversion apparatus of claim 1, wherein the hydrocarbon conversion apparatus includes four riser reactors.

7. The hydrocarbon conversion apparatus of claim 1, wherein the hydrocarbon conversion apparatus includes five riser reactors.

8. The hydrocarbon conversion apparatus of claim 1, wherein the hydrocarbon conversion apparatus includes six riser reactors.

9. The hydrocarbon conversion apparatus of claim 1, wherein the hydrocarbon conversion apparatus includes more than six riser reactors.

10. The hydrocarbon conversion apparatus of claim 3, wherein the feed distributor provides feed to each of the riser reactors in substantially equal streams through the feed heads.

11. The hydrocarbon conversion apparatus of claim 1, wherein the apparatus further comprises:
    (f) a fluidizing agent distributor in fluid communication with the catalyst retention zone, the fluidizing agent distributor being provided to feed a fluidizing agent to the catalyst retention zone to fluidize catalyst contained in the catalyst retention zone.

12. The hydrocarbon conversion apparatus of claim 11, wherein the apparatus further comprises:
    (g) a disperser positioned in the catalyst retention zone, the disperser being provided to disperse the fluidizing agent in the catalyst retention zone to fluidize the catalyst.

13. The hydrocarbon conversion apparatus of claim 12, wherein the disperser is a device selected from the group consisting of a grid, a screen and a perforated plate.

14. The hydrocarbon conversion apparatus of claim 1, wherein the catalyst return is positioned centrally to the riser reactors.

15. The hydrocarbon conversion apparatus of claim 1, wherein the hydrocarbon conversion apparatus includes a plurality of catalyst returns.

16. The hydrocarbon conversion apparatus of claim 15, wherein the apparatus further comprises:
    (f) a flow control device positioned on at least one of the catalyst returns.

17. The hydrocarbon conversion apparatus of claim 15, wherein the apparatus further comprises:
    (f) a flow control device positioned on each of the plurality of catalyst returns.

18. The hydrocarbon conversion apparatus of claim 1, wherein the separation zone further comprises a quiescent zone in which catalyst can be retained until the catalyst moves from the separation zone to the catalyst return.

19. The hydrocarbon conversion apparatus of claim 1, wherein the apparatus further comprises:
    (f) a catalyst regenerator in fluid communication with the hydrocarbon conversion apparatus.

20. The hydrocarbon conversion apparatus of claim 19, wherein the apparatus further comprises:

(g) a catalyst stripper in fluid communication with the hydrocarbon conversion apparatus and the catalyst regenerator.

21. The hydrocarbon conversion apparatus of claim 1, wherein the apparatus further comprises:
(f) at least one separation device positioned in the separation zone.

22. The hydrocarbon conversion apparatus of claim 21, wherein the at least one separation device is selected from group consisting of a cyclonic separator, a filter, an impingement device and combinations thereof.

23. The hydrocarbon conversion apparatus of claim 1, wherein each of the riser reactors has a cross sectional area of no greater than 12 m$^2$.

24. The hydrocarbon conversion apparatus of claim 1, wherein each of the riser reactors has a cross sectional area of no greater than 7 m$^2$.

25. The hydrocarbon conversion apparatus of claim 1, wherein each of the riser reactors has a cross sectional area or no greater than, 3.5 m$^2$.

26. The hydrocarbon conversion apparatus of claim 1, wherein each of the riser reactors has a height of from 10 meters to 70 meters.

27. The hydrocarbon conversion apparatus of claim 1, wherein each of the riser reactors has a width of from 1 meter to 3 meters.

28. The hydrocarbon conversion apparatus of claim 1, wherein each of the riser reactors has a cross sectional area and the cross sectional area of one of the riser reactors varies by no more than 20% from the cross sectional area of another of the riser reactors.

29. The hydrocarbon conversion apparatus of claim 28, wherein the cross sectional area of one of the riser reactors varies by no more than 10% from the cross sectional area of another of the riser reactors.

30. The hydrocarbon conversion apparatus of claim 29, wherein the cross sectional area of one of the riser reactors varies by no more than 1% from the cross sectional area of another of the riser reactors.

31. The hydrocarbon conversion apparatus of claim 1, wherein at least one of the deviating members comprises a tubular member providing a deviation angle of at least 45 degrees.

32. The hydrocarbon conversion apparatus of claim 1, wherein at least one of the deviating members comprises a tubular member providing a deviation angle of at least 90 degrees.

33. The hydrocarbon conversion apparatus of claim 1, wherein at least one of the deviating members comprises a 90 degree elbow.

34. The hydrocarbon conversion apparatus of claim 1, wherein the apparatus further comprises:
(f) a second plurality of riser reactors, each of the second plurality of riser reactors having first and second ends and a second center axis, wherein the separation zone includes a plurality of second inlets, each second inlet being oriented along a respective second center axis.

35. A hydrocarbon conversion apparatus, comprising:
(a) a plurality of riser reactors, each having a first end into which a catalyst can be fed and it second end through which the catalyst can exit the riser reactor;
(b) a separation 7.one provided to separate the catalyst from products of a reaction conducted in the hydrocarbon conversion apparatus, the separation zone including a plurality of inlets;
(c) a plurality of deviating members, each deviating member being a curved pipe, elbow or conduit device attached to the second end of a riser reactor so as to receive catalyst, products and unreacted feed and deviate flow of the catalyst, products and unreacted feed toward a respective inlet of the separation zone, wherein each of the plurality of riser reactors includes a center axis extending between the first and second ends thereof, and wherein the plurality of inlets are not oriented along the center axes of the riser reactors; and
(d) at least one catalyst return in fluid communication with the separation zone and the first ends of the riser reactors, the catalyst return being provided to transfer the catalyst from the separation zone to the first ends of the riser reactors.

36. The hydrocarbon conversion apparatus of claim 35, wherein each of the riser reactors has a height of from 10 meters to 70 meters.

37. The hydrocarbon conversion apparatus of claim 35, wherein each of the riser reactors has a width of from one meter to three meters.

38. The hydrocarbon conversion apparatus of claim 35, wherein each of the riser reactors has a cross sectional area of no greater than 12 m$^2$.

39. The hydrocarbon conversion apparatus of claim 35, wherein each of the riser reactors has a cross sectional area of no greater than 7 m$^2$.

40. The hydrocarbon conversion apparatus of claim 35, wherein each of the riser reactors has a cross sectional area or no greater than 3.5 m$^2$.

41. The hydrocarbon conversion apparatus of claim 35, wherein each of the riser reactors has a crass sectional area and the cross sectional area of one of the riser reactors varies by no more than 20% from the cross sectional area of another of the riser reactors.

42. The hydrocarbon conversion apparatus of claim 41, wherein the cross sectional area of one or the riser reactors varies by no more than 10% from the cross sectional area of another of the riser reactors.

43. The hydrocarbon conversion apparatus of claim 42, wherein the cross sectional area of one of the riser reactors varies by no more than 1% from the cross sectional area of another of the riser reactors.

44. The hydrocarbon conversion apparatus of claim 35, wherein the apparatus further comprises:
(e) a catalyst retention zone provided to contain catalyst which can be fed to the riser reactors.

45. The hydrocarbon conversion apparatus of claim 44, wherein the apparatus further comprises:
(f) a feed distributor including a plurality of feed heads, each head being positioned adjacent to the first end of a respective riser reactor.

46. The hydrocarbon conversion apparatus of claim 35, wherein the apparatus further comprises:
(e) a fluidizing agent distributor in fluid communication with the catalyst return, the fluidizing agent distributor being provided to feed a fluidizing agent to the catalyst return to fluidize catalyst contained in the catalyst return.

47. The hydrocarbon conversion apparatus of claim 46, wherein the apparatus further comprises:
(f) a regeneration apparatus in fluid communication with the hydrocarbon conversion apparatus.

48. The hydrocarbon conversion apparatus of claim 47, wherein the apparatus further comprises:
(g) a catalyst stripper in fluid communication with the regeneration apparatus.

49. The hydrocarbon conversion apparatus of claim 35, wherein at least one of the deviating members comprises a tabular member providing a deviation angle of at least 45 degrees.

50. The hydrocarbon conversion apparatus of claim 35, wherein at least one of the deviating members comprises a tabular member providing a deviation angle of at least 90 degrees.

51. The hydrocarbon conversion apparatus of claim 35, wherein at least one of the deviating members comprises a 90 degree elbow.

52. The hydrocarbon conversion apparatus of claim 35, wherein the apparatus further comprises:
(e) a second plurality of riser reactors, each of the second plurality of riser reactors having a first end into which a catalyst can be fed, and a second end through which the catalyst can exit the riser reactor and directly enter the separation zone.

53. A hydrocarbon conversion apparatus, comprising:
(a) a plurality of riser reactors, each having a first end for receiving catalyst mid a second end through which the catalyst and a product can exit the riser reactors;
(b) a separation zone having one or more separation devices for separating the catalyst and product exiting the riser reactors;
(c) a plurality of deviating members, each being a curved pipe, elbow or conduit device attached to the respective second end of each riser reactor so as to receive the catalyst and products exiting from each riser reactor and deviate flow of the catalyst and product toward the separation zone, wherein the deviating members are external to the separation zone; and
(d) a catalyst return in fluid communication between the separation zone and the first ends of the plurality of riser reactors.

54. The hydrocarbon conversion apparatus of claim 53, wherein the deviating member has a deviation angle of less than 90 degrees.

55. The hydrocarbon conversion apparatus of claim 53, wherein the deviating member has a deviation angle of from 10 to 90 degrees.

56. The hydrocarbon conversion apparatus of claim 53, wherein the deviating member has a deviation angle of from 30 to 90 degrees.

57. The hydrocarbon conversion apparatus of claim 53, wherein the deviating member has a deviation angle of from 45 to 90 degrees.

* * * * *